(12) United States Patent
Binkowski et al.

(10) Patent No.: US 8,447,738 B1
(45) Date of Patent: May 21, 2013

(54) COMPUTER SYSTEM AND METHOD FOR DE-IDENTIFICATION OF PATIENT AND/OR INDIVIDUAL HEALTH AND/OR MEDICAL RELATED INFORMATION, SUCH AS PATIENT MICRO-DATA

(75) Inventors: Edward S. Binkowski, New York, NY (US); Andrew Rosenberg, Astoria, NY (US); Moshe Rosenwein, Springfield, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 653 days.

(21) Appl. No.: 10/989,285

(22) Filed: Nov. 17, 2004
(Under 37 CFR 1.47)

Related U.S. Application Data

(60) Provisional application No. 60/520,385, filed on Nov. 17, 2003.

(51) Int. Cl.
*G06F 7/00* (2006.01)
(52) U.S. Cl.
USPC ............................................ 707/688
(58) Field of Classification Search
USPC ................................................. 707/101, 688
See application file for complete search history.

(56) References Cited

U.S. PATENT DOCUMENTS

| 6,278,999 | B1 | 8/2001 | Knapp |
| 6,397,224 | B1 | 5/2002 | Zubeldia et al. |
| 6,405,207 | B1 | 6/2002 | Petculescu et al. |
| 2002/0129031 | A1* | 9/2002 | Lau et al. ................ 707/101 |
| 2003/0220927 | A1* | 11/2003 | Iverson et al. ........... 707/100 |

OTHER PUBLICATIONS

"Preparing Public Use Data sets: guidance for ASPE Welfare Outcomes Grantees," ASPE Welfare Outcomes grantee meeting, ASPE Welfare Outcomes data files Work Group (Fall 2000).
Abowd, John M. and Simon D. Woodcock. "Disclosure Limitation in Longitudinal Linked Data." Confidentialitly, Disclosure, and Data Access: Theory and Practical Application for Statistical Agencies, pp. 215-277. (2001).
"Administrative Data Standards and Related Requirements." 45 CFR Part 160.
Bethlehem, Jelke G. et al. "Disclosure Control of Microdata." Journal of the American Statistical Association, 85(409):38-45. (1990).
Dalenius, Tore and Steven P. Reiss. "Data-Swapping: A Technique for Disclosure Control." Journal of Statistical Planning and Inference, 6:73-85. (1982).
Govoni, John P. and Preston J. Waite. "Development of a Public Use File for Manufacturing." pp. 300-302.

(Continued)

*Primary Examiner* — Apu Mofiz
*Assistant Examiner* — Ajith Jacob
(74) *Attorney, Agent, or Firm* — Husch Blackwell LLP

(57) ABSTRACT

A computer-implemented method de-identifies data collected for patients. IN at least one embodiment, the method comprises the sequential, non-sequential and/or sequence independent steps of providing information representative of at least one patient, at least one medical characteristic associated with at least one patient thereto, and a geographic area of the at least one patient, and providing at least one organizational structure for organizing medical characteristics. The method also includes associating the at least one organizational structure with at least one geographical area and at least one medical characteristic, and aggregating, in the at least one organizational structure, said information by medical characteristic and the at least one geographic area therein. Various alternative embodiments are additionally disclosed.

3 Claims, 11 Drawing Sheets

OTHER PUBLICATIONS

Greenberg, Brian and Laura Voshell. "The Geographic Component of Disclosure Risk for Microdata." Report No. Census/SRD/RR-90/13 for the Bureau of the Census Statistical Research Division. (Oct. 5, 1990).

Griffin, Richard A. and Linda Flores-Baez. "Disclosure Avoidance for the 1990 Census." Proceedings of the Section on Survey Research Methods. (Aug. 6-10, 1989).

Health Insurance Portabililty and Accountability Act of 1996. Public Law 104-191. 104th Congress. (Aug. 21, 1996).

Interagency Confidentiality and Data Access Group. "Checklist on Disclosure Potential of Proposed Data Releases." Statistical Policy Office. (Jul. 1999).

Kim, Jay. "Subpopulation Estimation for the Masked Data." Proceedings of the Section on Survey Research Methods. (Aug. 6-9, 1990).

McGuckin, Robert H. and Sang V. Nguyen. "Use of 'Surrogate Files' to Conduct Economic Studies with Longitudinal Microdata." pp. 193-211.

Mugge, Robert H. "Issues in Protecting Confidentiality in National Health Statistics." Proceedings of the Section on Survey Research Methods. (Aug. 15-18, 1983).

Skinner, C. J. "On identification disclosure and prediction disclosure for microdata." Statistica Neerlandica, 45(1):21-32. (1992).

Strudler, Michael et al. "Protection of Taxpayer Confidentiality with Respect to the Tax Model." Proceedings of the Section on Survey Research Methods. (Aug. 18-21, 1986).

Subcommittee on Disclosure Limitation Methodology, Federal Committee on Statistical Methodology. "Report on Statistical Disclosure Limitation Methodology." Statistical Policy Office, Working Paper 22. (May 1994).

Sullivan, Gary and Wayne A. Fuller. "The Use of Measurement Error to Avoid Disclosure." Proceedings of the Section on Survey Research Methods. (Aug. 6-10, 1989).

Sweeney, Latanya. "Guaranteeing Anonymity when Sharing Medical Data, the Datafly System." pp. 51-55. (1997).

\* cited by examiner

COMPUTER SYSTEM AND METHOD FOR DE-IDENTIFICATION OF PATIENT AND/OR INDIVIDUAL HEALTH AND/OR MEDICAL RELATED INFORMATION, SUCH AS PATIENT MICRO-DATA

RELATED APPLICATIONS

This application claim priority to, and is a non-provisional patent application of, U.S. Provisional Patent Application Ser. No. 60/520,385 filed Nov. 17, 2003, entitled "Method and System for De-Identification of Patient Microdata," which is assigned to the assignee of this application and is incorporated herein by reference.

BACKGROUND OF THE INVENTION

1. Field of the Invention

The present invention is directed to computer-related and/or assisted systems, methods, and computer program devices for facilitating efficient and effective use of patient and/or individual related information. More particularly, the present invention relates to techniques for facilitating efficient and effective use of patient and/or individual related information such as medical and/or health related information in compliance with Health Insurance Portability and Accountability Act (HIPAA) of 1996.

2. Description of the Related Art

Some prior attempts have been made in unrelated fields in the healthcare industry to protect patient related information for various reasons. The prior art has not addressed what can be shared or disclosed based on HIPAA regulations.

The Knapp patent, U.S. Pat. No. 6,278,999, incorporated herein by reference, discloses an information management system for personal health digitizers (see FIG. 1) wherein a centralized database 100 collects and stores monitoring data from a large number of individuals and processing elements 101-108 perform statistical analysis of the collected data on a per consumer, population segment, or query-specific basis. The database is architected in a hierarchical manner to limit users' access to only that prepartitioned segment of the collected data that the particular class of user is authorized to analyze. Data is gathered from remotely located sources T1-Tn, comprised of individual consumers using Personal Health Digitizers to take readings on themselves or family members and downloading the data to the information management system IMS via a personal computer modem and Internet browser T1-Tn communicating with an interactive website WS and its data router DR. Alternatively, data can be communicated to the information management system IMS via consumer terminal equipment T1-Tn and the Pubic Telephone Switched Network PTSN.

Data from Personal Health Digitizers communicated to the information management system IMS can be accessed by those consumers who communicate the data via terminal equipment T1-Tn, by health care providers at their terminal equipment and servers S1-Sm, by institutions via their terminal equipment and servers I1-Ij, by medical practitioners, and others whom the consumer designates. These users, broken down into classes, can access the information management system IMS and its analysis functions only to the extent authorized by the consumer. Access control via the communication network PTSN is enforced by the use of database filters 103-106 architected to provide customized access to selected classes of users. The granularity of the data made available to the various classes of users is further selected and limited to prevent the users from deriving information about the consumer population that they are not entitled to receive. Data processing algorithms 108 operate on the raw physiological data collected from individual consumers and produce additional data that aids in identifying potential physiological problems. Interpretive processing systems 107, either standard software database processes or neuromorphic systems, such as expert systems or neural networks, use pattern recognition operations to analyze the collected data for correlations with regard to cohort-based sets of criteria identified.

The Petculescu patent, U.S. Pat. No. 6,405,207, incorporated herein by reference, discloses a multidimensional, multilevel database system (see FIG. 2) wherein query syntax is used to operate a database engine 204 that extracts and aggregates in a report 206 only the data from those items that are specified in the query. A database client 201 provides facilities for multiple users to specify the data to be provided from the database 205. The query 202 then passes to query processor 203, where it is converted into sequenced operations performed by an execution engine 204 to obtain the specified data. The execution engine 204 then aggregates data into a report which the database client 201 displays. The query processor 203, execution engine 204, and database 205 are typically components residing in one or more central computers accessed by query software operating from individual personal computers that serve as database clients 201.

The Zubelida patent, U.S. Pat. No. 6,397,224, incorporated herein by reference, discloses a system (see FIG. 3) for anonymously linking multiple data records 352 by double-encoding and assigning an anonymization code to data elements that can be used to identify an associated individual. Data records 352 are stored within an input database 354, either conventional or computerized. Each record includes a plurality of identifying elements 356 including, for example, name birth date, address, ZIP code, telephone number, healthcare identifier, and the like. Identifying elements 356 of the data records 352 are encoded by two or more modules 358 that can be combined or integrated into a single software application or device. The identity reference encoding modules 358 operate in multiple steps. First, identifying elements 356 of a data record are broken into subsets 362. The identifying elements are then translated into encoded identity references 360 by applying a cryptographic hash function or other hashing scheme, such as symmetric or public key cryptographic algorithms. This process can be repeated one or more times if the system 350 contains one or more additional identity reference encoding modules 358, with the goal of reducing the probability of an unintended collision where two subsets 362 share the same encoded identity reference 360.

The system 350 also includes an anonymization code database 368 that stores anonymization code 366 assignments (for example, serial numbers) associated with encoded identity references 360 and in turn a particular individual, group, or population. An anonymization code lookup module 364 utilizes a database query module 370 to retrieve the anonymization code 366 for each of the encoded identity references 360. If no code is associated with a particular reference, an anonymization code assignment module 372 uses an anonymization code generation module 374 to assign a new, unique anonymization code 366 to each of the encoded identity references 360 that describe an individual, group or population. A database update module 376 is used to ensure that the assigned anonymization code 366 corresponds to the multiple encoded identity references 360 associated with an individual, group, or population. Finally, an anonymization code insertion module 380 inserts the assigned anonymization code 366 into the anonymized data record 382. The inclusion of an identifying element removal module 378 is optional.

However, to the knowledge of the inventors, no attempts have been made to aggregate information about population, drug usage, health and/or medical related information in a manner that can be legitimately used. In addition, no attempts appear to have been made to aggregate health and/or medical related information in compliance with HIPAA regulations and/or in a manner that can be used to assist healthcare providers, health management companies, in research, healthcare and/or marketing, for example, in a small geographic area.

SUMMARY OF THE INVENTION

The present invention is a method and/or computer-implemented system to provide patient medical information in a way that in at least one embodiment, for example, conforms to HIPAA regulations regarding maximum re-identification risk. The invention is based on aggregation methods. The first aggregation method uses geographic proximity among patients, the second uses similarity of medical information. Other aggregation methods may be combined and/or utilize the overall aggregations process developed in the present invention to de-identify geographic, individual or patient-related data and/or conform to HIPAA regulations.

The first aggregation method, while maintaining low overall re-identification risk, also dramatically reduces the range of the risk of re-identification between zip codes. The second aggregation method provides more useful information than HIPAA "safe harbor" regulations, while also resulting in a much lower risk of re-identification.

The aggregation based on geographic proximity in the present invention includes as a first step ensuring that the input data is valid. This process begins by identifying patient records without zip codes. Those patient records without a zip code that cannot be corrected for are removed and/or filtered from the database. Next, the first unmerged zip code and its corresponding population is retrieved. If the population of the zip code is greater than the minimum needed to conform to HIPAA regulations (the safe limit), then the zip code is left alone. If the population is less than the safe limit, the zip code is then combined with nearby zip codes until the geographic area is greater than the safe limit. This is repeated until the aggregation process for all zip codes is finished.

The second method of aggregation, which is based on aggregating across medical information, has an initial process of clustering, followed by coding, and finally a process for providing the de-identified data. The process is implemented on a computer that is connected to a patient profile database, a cluster database, and a database of patient medical information. The clustering part of the de-identification process is intended to place the medical information into a hierarchy that is meaningful to the intended user of the de-identified information. The coding process is the second part of the de-identification method. The process of coding extracts the necessary information from the patient medical information database and the patient profile database to determine the prevalence of a medical characteristic in a zip code. This level of usage by zip code is then stored into the cluster database. The final part of the de-identification method is to receive request for zip codes or medical characteristics and respond with the appropriate de-identified information.

In one embodiment of the invention, a computer-implemented method for de-identifying data collected for patients, includes providing information representative of at least one patient, at least one medical characteristic associated with at least one patient, and a geographic area. This method also includes associating at least one patient with at least one geographic area, and creating at least one aggregated geographic area capable of de-identifying information through aggregating zero or more smaller geographic areas. Finally, the method aggregates information by medical characteristic and associates this information with the aggregated geographic area capable of de-identifying information In another embodiment of the invention, a computer-implemented method for de-identifying data collected for patients includes providing information representative of at least one patient, at least one medical characteristic associated with at least one patient, and a geographic area of the at least one patient. This method also provides at least one organizational structure for organizing medical characteristics, then associating the organizational structure with at least one geographical area and at least one medical characteristic. Information is then aggregated by the at least one medical characteristic and the at least one geographic area therein into the organizational structure.

In another embodiment of the invention, a computer-implemented method assesses compliance of de-identified data with data de-identification requirements, which includes safe harbor. The method includes the steps of quantifying a safe harbor risk for at least one data set by applying the safe harbor to the at least one data set, and then also applying at least one method of de-identifying data to the at least one data set. The method next compares the re-identification risk of the at least one de-identifying method to the safe harbor risk to determine whether the re-identification risk is lower than the safe harbor risk.

In another embodiment of the invention, two previous embodiments are combined together. The embodiment of aggregating medical information with an organizational structure is advantageously combined with the embodiment based on aggregating smaller geographic areas.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be

DETAILED DESCRIPTION OF THE INVENTION

Figure 1:
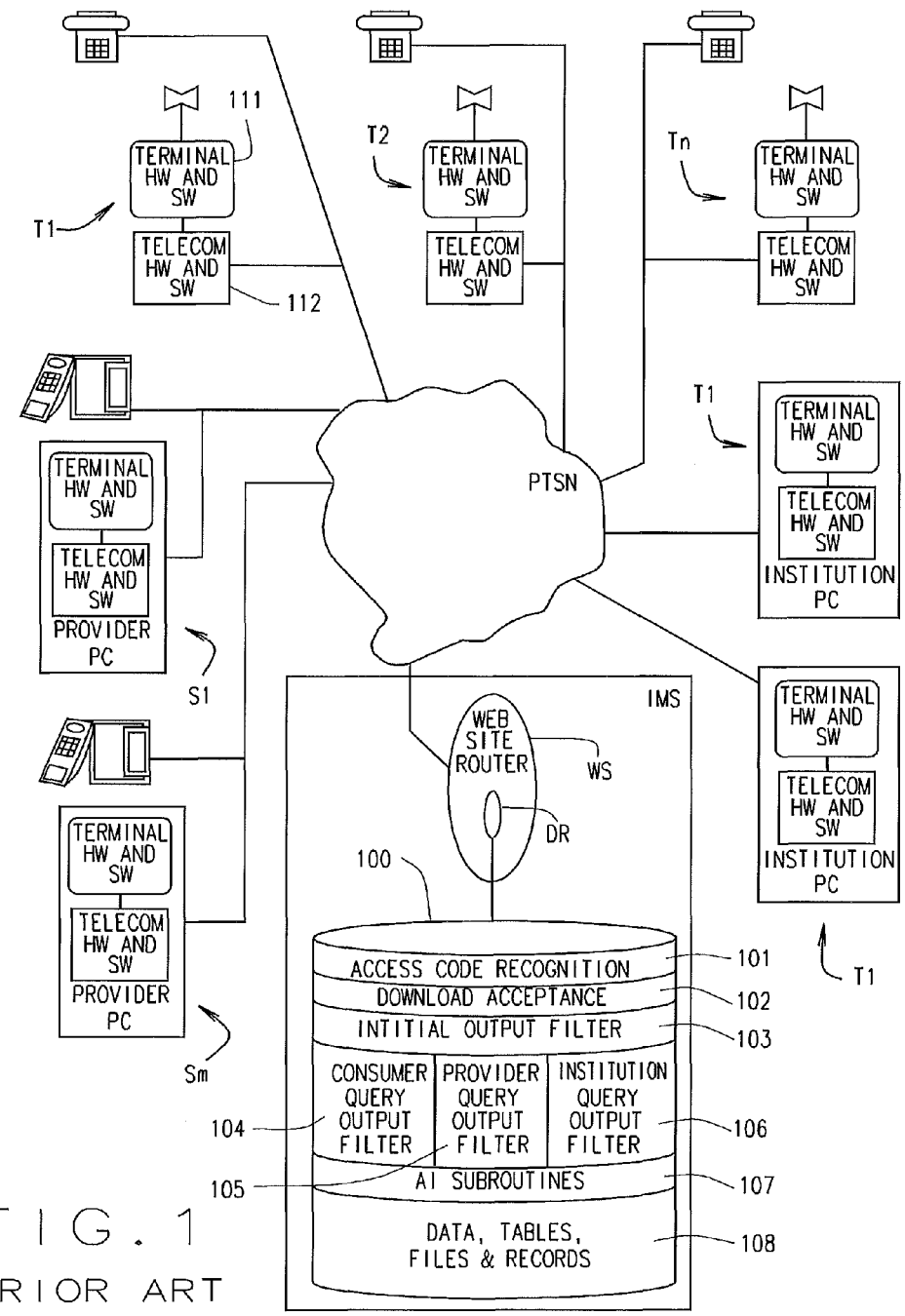
FIG. 1 is an illustration of a prior art information management system for personal health digitizers.
Figure 2:
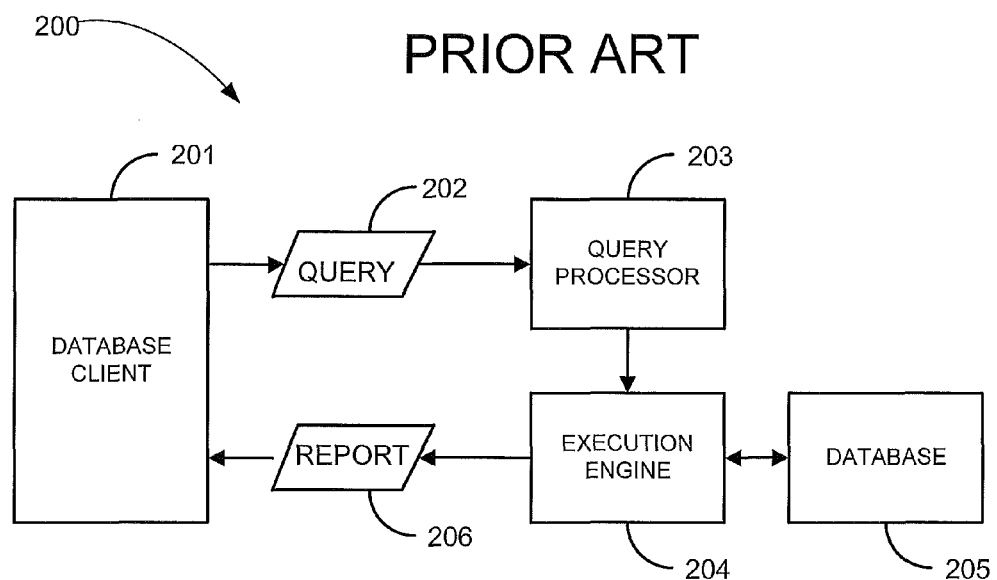
FIG. 2 is an illustration of a prior art multidimensional, multilevel database system.
Figure 3:
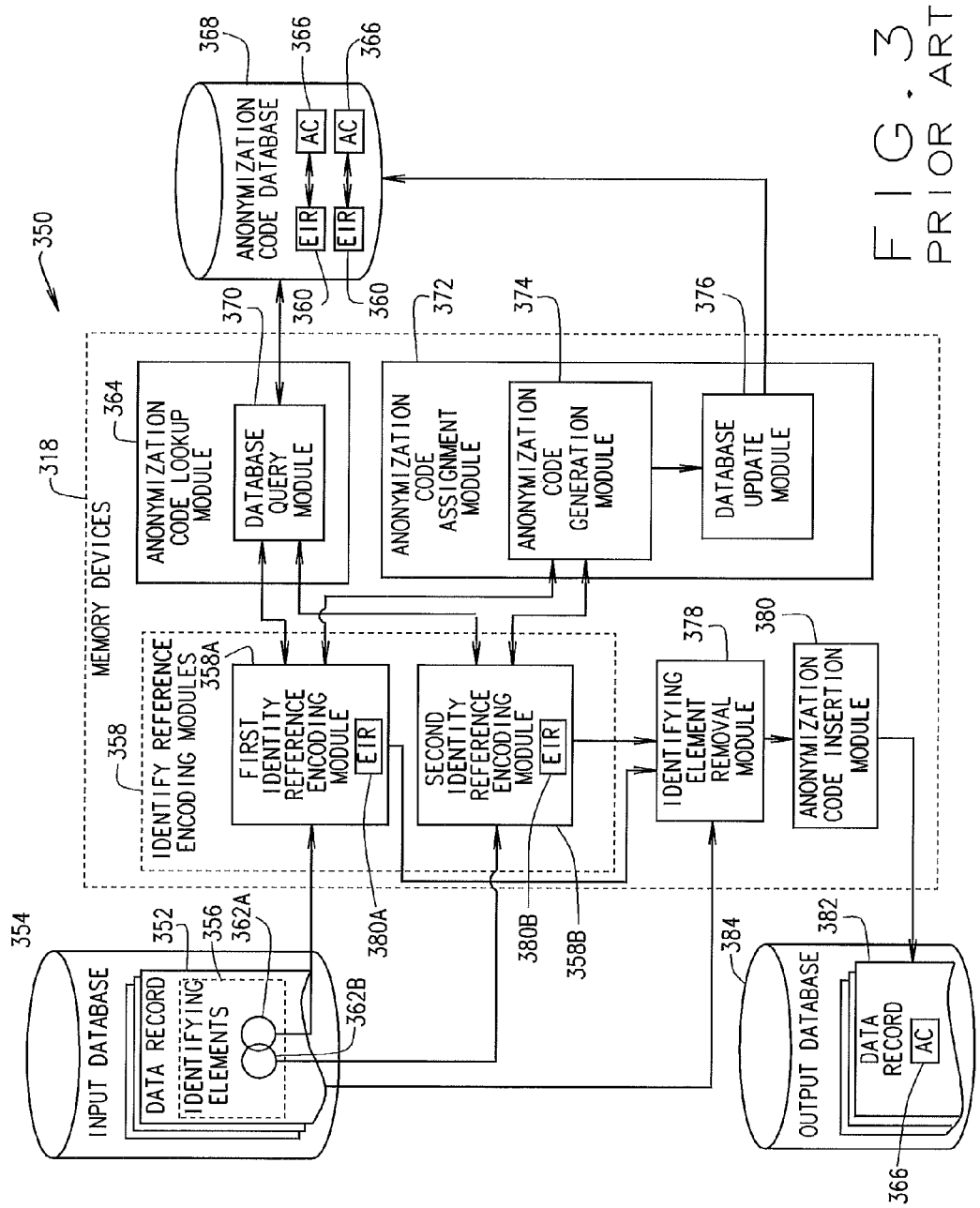
FIG. 3 is an illustration of a prior art system for anonymously linking multiple data records.

The following detailed description includes many specific details. The inclusion of such details is for the purpose of illustration only and should not be understood to limit the invention. Throughout this discussion, similar elements are referred to by similar numbers in the various figures for ease of reference. In addition, features in one embodiment may be combined with features in other embodiments of the invention.

The present invention is a method and/or computer-implemented system to provide patient medical information in a way that in at least one embodiment, for example, conforms to HIPAA regulations regarding maximum re-identification risk. The invention is based on aggregation methods. The first aggregation method uses geographic proximity among patients, the second uses similarity of medical information. Other aggregation methods may be combined and/or utilize the overall aggregations process developed in the present invention to de-identify geographic, individual or patient-related data and/or conform to HIPAA regulations.

The first aggregation method, while maintaining low overall re-identification risk, also dramatically reduces the range of the risk of re-identification between zip codes. The second aggregation method provides more useful information than HIPAA "safe harbor" regulations, while also resulting in a much lower risk of re-identification.

The aggregation based on geographic proximity method in the present invention, includes as a first step, providing de-identified data that is useful for marketing or other purposes, to ensure that the input data is valid. This process begins by identifying patient records without zip codes. Those patient records without a zip code that cannot be corrected for are removed and/or filtered from the database. The remaining records are treated as any other records that originally had zip codes. In an actual test database of patient information, records with out zip codes made up about 38.6% of the total patient records. The removal of any records without a zip code advantageously results in an under estimate of re-identification. It is less likely that a patient could be identified with public records, when that person does not have a zip code, as compared to one who does.

One group of records in the test database with missing zip codes, belonged to zip codes that could not be found in the 2000 Decennial Census. This accounted for 19.2% of zip codes but only 1.9% of patients of the baseline population. This can occur because these are new zip codes created since the last census and because the Census Bureau and the United States Post Office differ in their assignment of zip codes.

More information about how the zip code assignment differs between the United States Post Office and the Census Bureau may be found at http://pe.usps.gov/text/dmm/1606.htm and http://www.galaxymaps.com/wezipchg.htm. The information found at these sites was used to map the 2000 census data into the zip codes used by customers, which are United State Post Office zip codes. This mapping is preferred because not only is it more forward looking and current, but because it also maximizes the estimated risk of re-identification. It disaggregates the Census data into the United State Post Office zip codes rather than aggregating the United State Post Office data into Census zip codes. This disaggregation was also used to correct for patients who lived in new zip codes that had been formed out of previously existing zip codes.

The disaggregation proceeded as follows.

$C_i$=Census population in $i^{th}$ zip code, and $P_{ij}$=Population in $j^{th}$ zip code formerly part of $i^{th}$ zip code, then $C_{ij}=C_i*P_{ij}/\Sigma_j P_{ij}$ (summing over all zip codes formerly part of the $i^{th}$ zip code)

In general, a population was assigned to new zip codes that split the population of the old zip code equally among the new ones created out of it. It was assumed that when a new zip code was formed out of an old one, that the new zip code shared equally in the population. As before, this works to over estimate re-identification risk, since new zip codes areas are growing more quickly than already established zip codes, and therefore, ought to be assigned some proportionately higher degree of the population.

Another group of invalid zip codes, referred to as non-residential areas, are not associated with any geographic area. Instead they represent a specific office building, post office, of post office box. Very few of these zip codes were found in an actual database.

Incorrect zip codes are another source or invalid data. One ease of this can be detected when an unrealistically high percentage of the population of are customers. Sometimes this means, an insurance carrier has used its zip code for the zip code of all its patients. A two step search was used to find these incorrect zip codes. The first step was to determine individual zip codes where an insurance company had significantly high over-representation. The second step was to decide if within such a zip code, whether a particular insurance carrier had an unrealistically high share of the total patient records. For the first determination, a straightforward studentization of the insurance company population was used as shown below:

$C_j$=Census population for $j^{th}$ zip code $B_j$=Insurance company patient population for $j^{th}$ zip code $Exp_j$=*(Total B Pop)/(Total Census Pop)

$Score=(B_j-Exp_j)/sqrt(Exp_j)$

This determination was made, for example, on a purely statistical basis, although additional factors may also be utilized in the first determination. The second determination—identification of possibly aberrant carriers within an overrepresented zip code—was based on the expectation that carriers' shares of the insurance companies patients within a zip code should follow an exponential distribution given a uniform distribution of carriers' population. Since many, if not most, carriers are, however, geographically centered, it is likely that a given carrier might have the bulk of their business within a particular zip code.

Figure 12:
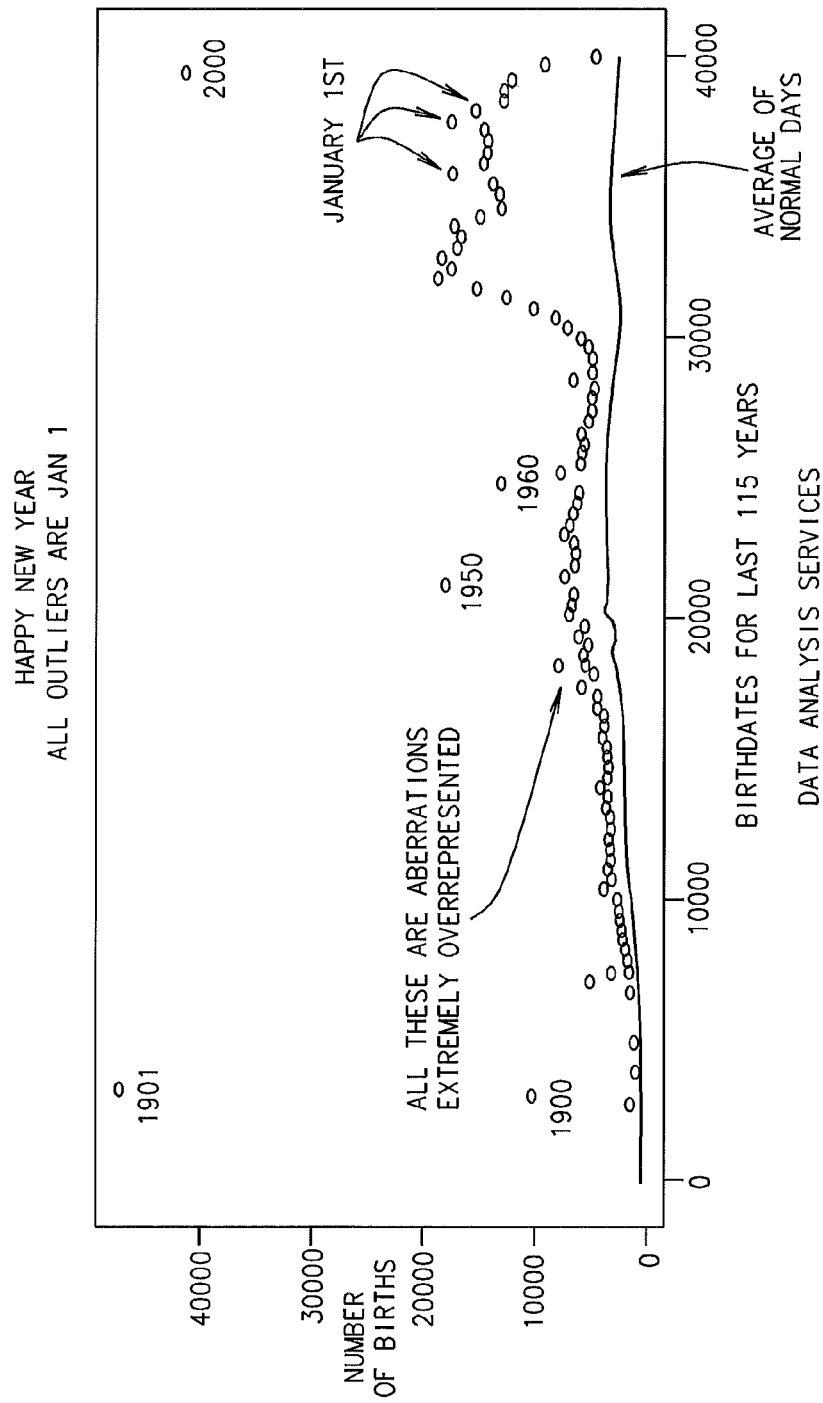
FIG. 12 is a diagram illustrating anomalous birth dates in the patient database.

Incorrect birthdates were another source of invalid data. These were removed to the extent possible. For instance, the current database has 4 times more centenarians than the 2000 Decennial Census recorded, and also contained a few individuals whose birthdates were in the future. Other dates, such as January 1st of every year, and the first and last day of each month, are also overrepresented. To correct for this, the residuals were calculated from a smooth trace running through all the data. One exemplary representation of the data is plotted, for example, in FIG. 12.

The first method of aggregation for reducing re-identification risk is based on geographic proximity. The HIPAA "safe harbor" regulations require any geographic indicator to contain at least 20,000 people, and recommend that zip codes be aggregated to the 3 digit level to provide this floor. This level of aggregation has been determined to be generally unnecessary except for a very few zip codes. The present invention advantageously preserves more information than HIPAA "safe harbor" regulations by, for example in one embodiment, making geographic areas more uniform in population size. This is accomplished in one embodiment by merging zip codes only when necessary to achieve a population size whose risk of re-identification would conform to HIPAA "safe harbor" regulations.

The level of risk allowed by HIPAA "safe harbor" regulations was determined by creating a regression model based on the published re-identification risk numbers in the HIPAA legislation. A population of 500,000 can have an re-identification risk of 0.4%, a population of 100,000 can have an identification risk of 3%, and a population of 25,000 can have an identification risk of 10%, these numbers came from a study done by the National Center for Health Statistics. A log linear regression model was created based on these numbers for estimating re-identification risk:

Re-identification probability=
$10^{(-0.66048-0.07868*sqrt(n/1000))}$

From this model it is estimated that the 2000 Decennial Census had an average re-identification risk of 0.85%, with a maximum risk of 8.77% for any one zip code. The estimate for the 1990 Decennial census was an average re-identification risk of 1.01%. The present invention here advantageously results in less risk than the HIPAA legislation models would have resulted in for the 2000 Census data when using the aggregation processes described herein.

This re-identification risk estimate can be made more accurate by accounting for the imperfections in actual data. For example in one embodiment, this imperfection in data due to reasons explained above lower the re-identification risk by about 10%. This is because missing zip anomalies accounted for 9.11% of the data, incorrect zip codes inserted by the insurance accounted for 3.48%, age and birth date anomalies for 1.73%, and age distribution for 3.87%. The overall effect of this is (1−3.48%)*(1−1.73%)*(1+3.87%)/(1+9.11%)= 90.30%, or lowering re-identification risk by 10%.

In one embodiment of the present invention, the estimated re-identification risk was 0.16%. This was derived from the baseline patient population containing 448,883 unique 5 digit zip code and birth year combinations. This resulted in a naive re-identification risk of 0.72%. But the population of a particular medical provider is not that same as the entire population. It was 4.62 smaller that the national population, meaning the estimated re-identification risk was 0.72%/4.62=0.16%, since not ever patient record will also be unique in the national population. This low rate of re-identification means gender information could also be added.

Aggregating to the 3 digit level for zip codes is generally unnecessary to meet the level of risk allowed, except for a very few zip codes. Matching records using zip code and birth year results in a very low risk of re-identification even when using the entire 5 digit zip code. This hypothesis was validated using actual public information along with actual patient information. Software and data was purchased from Pallorium corporation, along with their "People Finder" software for the states of New York and Texas. The data CDs contain a combination of driver's license, voter registration, and property tax records, together with name, address phone number and birth date for each record. This information was compared to the information in the patient database to see how many unique matches occurred, which meant someone could be re-identified. The results are shown in the table below, showing the experimental re-identification risk of 0.01%. At that risk level, gender information can easily be added in compliance with HIPAA "safe harbor" regulations, but birth month, which would increase risk by 12 times, cannot. This means where age, gender, and 5 digit zip code are the only fields in a record matched in a public use data file, de-identification risk can meet HIPAA "safe harbor" regulations.

TABLE

| Actual Re-Identification Risk for 5-Digit Zip and Birth year | | | | |
| --- | --- | --- | --- | --- |
| | New York | (%) | Texas | (%) |
| Patient database | 2,844,109 | | 3,524,857 | |
| Unique records patient database | 24,490 | 0.86% | 26,321 | 0.75% |
| Public: Found | 15,847 | 0.56% | 18,534 | 0.53% |
| Public: "Unique" | 1,096 | 0.04% | 2,038 | 0.06% |
| Public: True Match | 299 | 0.01% | 344 | 0.01% |
| 2000 Census (estimated risk) | | 0.84% | | 0.84% |

Figure 11:
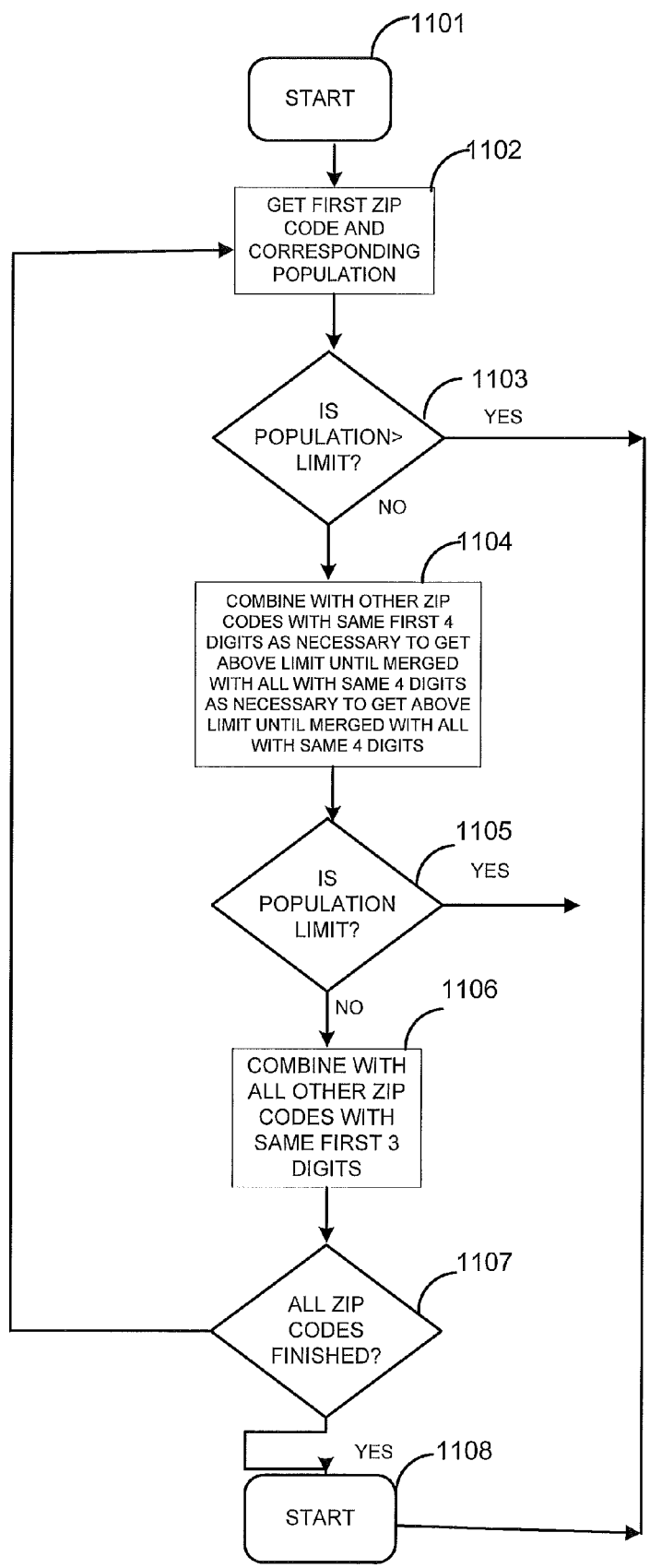
FIG. 11 is a flow chart illustrating the steps performed in aggregating medical information based on zip code

Turning to FIG. 11, the process of aggregation based on geographic proximity is described. In FIG. 11, the process starts by retrieving the first unmerged zip code and its corresponding population 1102. If the population of the zip code is greater than the minimum needed to conform to HIPAA regulations (the safe limit), then the zip code is left alone 1103. For example, with one embodiment of the invention, which contained a database with the prescription purchases of over 100 million patients, a zip code with 250,000 people is sufficiently large to conform to HIPAA "safe harbor" regulations. If the population is less than the safe limit 1103, the zip code is then combined with nearby zip codes containing the same first 4 digits 1104, until the geographic area is greater than the safe limit 1105, 1106. In one embodiment of the invention, this process of combining zip codes was done using a "greedy" algorithm. If the population is still not above the safe limit after merging with all zip code with the same first 4 digit, then it is combined with nearby zip codes with the same first 3 digits 1107 until it is greater than the safe limit 1108, 1109. Regardless, if after merging with all other zip codes with the same first 3 digits the population is greater than the safe limit, the aggregation process is finished. This is repeated until the aggregation process for all zip codes is finished 1110. Other modified version of this process may also be used in the present invention and/or in combination. For example, instead of combining population with the same first 3 digits, other populations may be added to increase the population for the safe limit.

Figure 4:
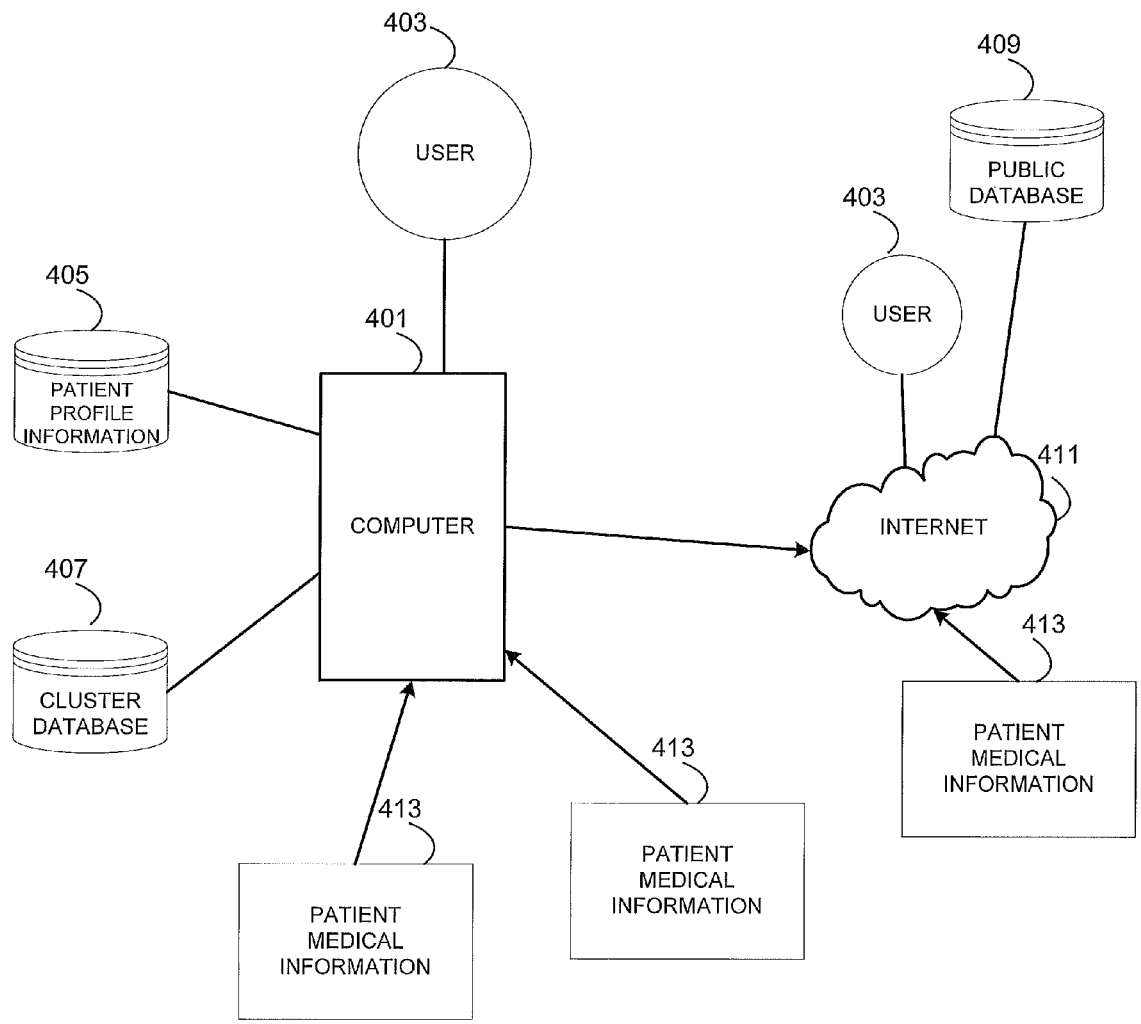
FIG. 4 is a block diagram illustrating the overall system layout for aggregation based on medical information.

The second method of aggregation, which is based on aggregating across medical information, has an initial process of clustering, followed by coding, and finally a process for providing the de-identified data. The overall design of aggregation based on medical information is shown in FIG. 4. The process is implemented on a computer 401 that is connected a patient profile database 405, a cluster database 407, and a database of patient medical information 413. The patient profile database stores profile information about patients that is partially independent of their medical information. This includes information like name, address, zip code, etc. The patient medical information database contains their medical information, which could be information such as prescription purchases, current medical conditions, and/or genetic traits. Finally, the cluster database 407 stores the information that is produced during the clustering and coding parts of the aggregation process.

If additional information is needed during any phases of the aggregation process, it can be accessed, for example, at public databases 409 that are connected through the Internet 411. Information such as census data, population studies, and surveys, can be useful in preparing and filtering patient profile and patient medical information databases.

The clustering part of the de-identification process is intended to place the medical information into a hierarchy that is meaningful to the intended user of the de-identified information. For one embodiment of the invention, the medical information comprised drugs that were placed into a hierarchy based on similarity of drugs. Other types of medical information such as specific medical conditions or genetic traits may optionally be placed into their own hierarchy. For one embodiment of the invention, based on drug usage, prescription purchases of all drugs were placed into a hierarchy that began with the standard 79 second level categories of the uniform formulary therapeutic classification scheme. This is a uniform system of drug classification that many health insurance plans have adopted. These 79 second level categories are then advantageously grouped into one of 30 third level clusters. Those 30 clusters are then grouped into one of 13 fourth level clusters, and finally, those 13 clusters are grouped into one of 4 meta-clusters. In one embodiment of the invention, a single third level cluster optionally contains beta-blockers, direct acting miotics, glaucoma drugs, and sympathomimetics. A single meta-cluster optionally contains sub-clusters like antihistamines, migraine medication, and immunosuppressants.

Figure 5:
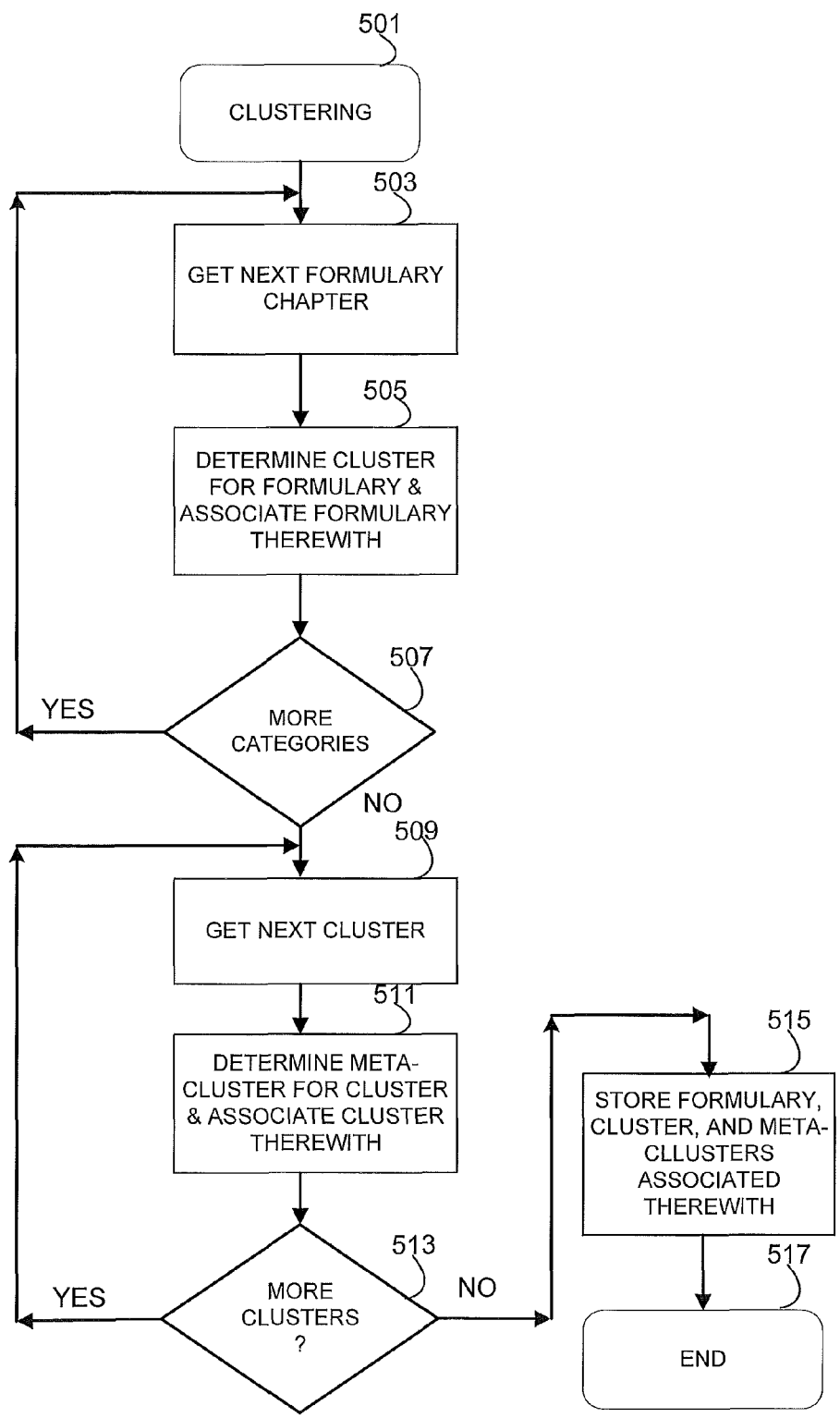
FIG. 5 is a flow chart illustrating the steps performed in organizing the medical characteristics into a hierarchy.

As illustrated in FIG. 5, the clustering process begins by associating the medical information with the proper lowest level category 503. The next step in the process, grouping the lowest level categories into the higher level clusters is done, for example, by determining points of similarity that exist between the separate levels 505. This determination is made by using an agglomerative clustering algorithm. The algorithm is one which places the two closest objects together in one cluster; then the two next closest objects (which can themselves be clusters), and so on, until all objects are in one large cluster.

Once all the second level categories have been associated with higher level clusters 507, they are then processed 509 and associated with one of the meta-clusters 511. The grouping into the meta-clusters is more straightforward because of the breadth of the categories. In one embodiment of the invention 4 meta-clusters were used: acute, chronic, dermatological, and miscellaneous, although any number of meta-clusters may be used. After the clusters have been associated with a meta-cluster 513, all this information regarding the hierarchy structure is stored 515 in the cluster database. The clustering process is then finished 517.

Figure 6:
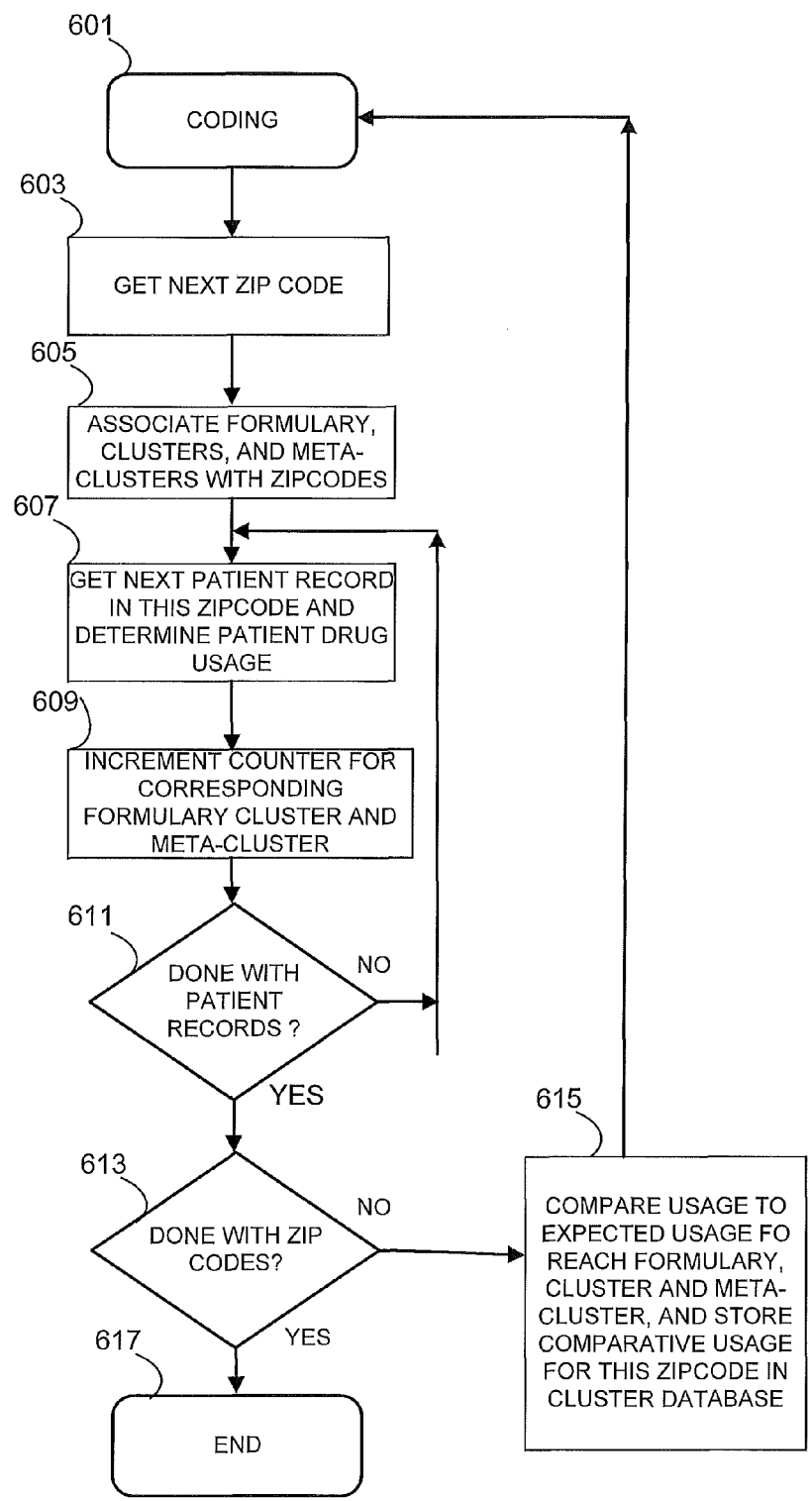
FIG. 6 is a flow chart illustrating the steps performed in coding the information contained in the patient records.

The coding process, shown in FIG. 6, is the second part of the de-identification method. It combines, in one embodiment, the patient medical information database, the patient profile database, and the cluster database. The process of coding extracts the necessary information from the patient medical information database and the patient profile database to determine the prevalence of a medical characteristic in a zip code. In one embodiment of the invention, involving a prescription database, the information extracted corresponds to whether there is a high/average/low usage for a drug in a zip code. This level of usage by zip code is then stored into the cluster database. The specific combination of high/average/low usage may be determined by the application, user, drug, condition, and the like.

The process of coding 601 retrieves a zip code 603, it then associates one path of the cluster hierarchy with the zip code 605. In one embodiment of the invention, an association is performed with one combination of a second level category, a third and fourth level cluster, and a meta-cluster. Additional associations and/or combinations may optionally be used. The process of retrieving zip codes and associating them with the hierarchy is automatic since each zip code is eventually associated with each possible path. The next step is to retrieve a patient profile record from the zip code, and the corresponding record from the patient medical information database 607. A counter is then incremented that corresponds to the characteristic of the patient's medical information that is of interest 609. In one embodiment of the invention, the counters for a drug are incremented if a patient bought a prescription for that drug. This is optionally continued until all patient profile records in the zip code have been processed 611. The usage in the zip code is then compared to the expected usage for the zip code, and the result of high/average/low is stored in the cluster database 615. This process continues until all zip codes have been processed 613. The coding process is then finished 617. Alternative combinations or sequences of the above described coding process may optionally be used.

Figure 7:
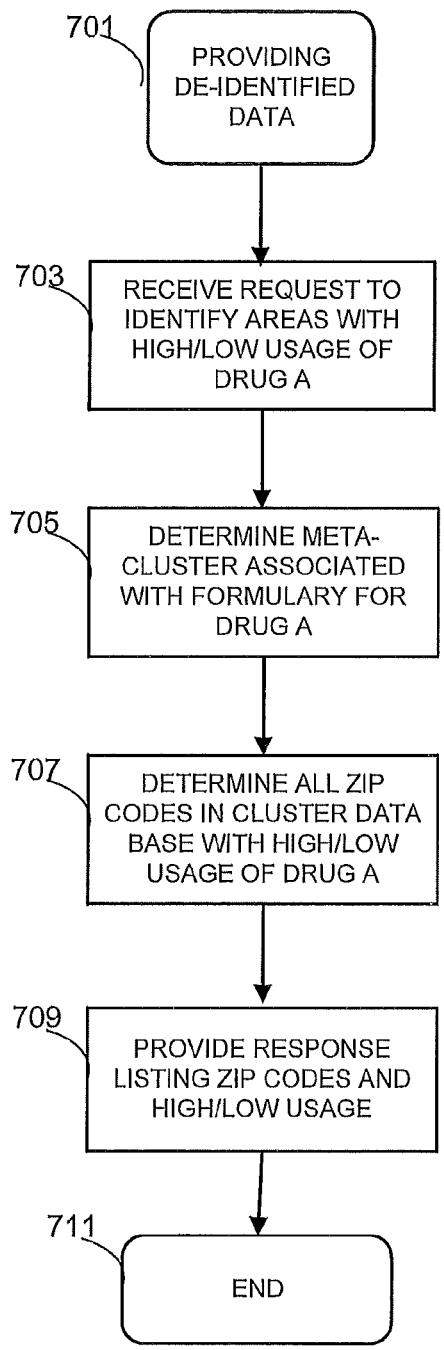
FIG. 7 is a flow chart illustrating the steps performed in providing the de-identified information in response to a specific request.

The final part of the de-identification process is shown in FIG. 7. This phase retrieves the de-identified data in response to a request to identify an area with a high/average/low level of a medical characteristic 701. The process begins by receiving a request for a characteristic 703, then determining what path in the hierarchy that characteristic has been associated with 705. Next, for the requested medical characteristic, the level of prevalence for all zip codes is retrieved 707. In one embodiment of the invention, this corresponds to the amount of a drug purchased in that zip code. This retrieval process can be accomplished by retrieving all records for a characteristic, since in the previous clustering process a prevalence level for each zip code of a medical characteristic was stored in the cluster database associated with a hierarchy path. Finally, a response listing is provided 709, and the process is finished 711.

Many other types of response listings are also possible after the clustering and coding processes have organized information in the database. For instance, instead of returning a prevalence level by zip code for a medical characteristic, the opposite process could be easily done. The user could make a request for the prevalence level of a medical characteristic for a zip code, and that information could be returned for each level in the cluster hierarchy. In addition, alternative and/or modified steps can be used to filter cluster, and/or aggregate information to appropriately de-identify information in accordance with the present invention.

Figure 8:
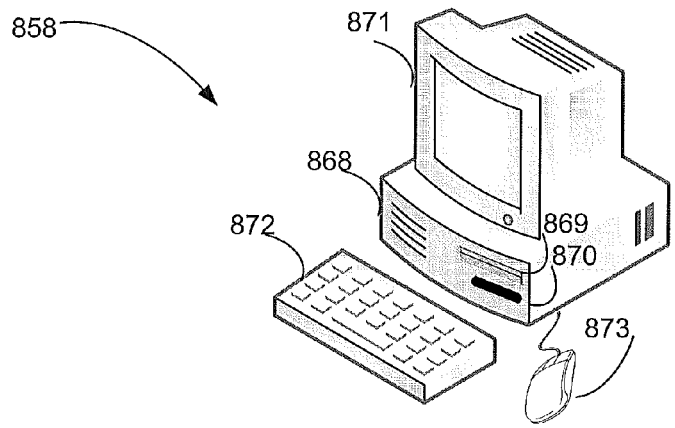
FIG. 8 shows a block diagram of a computer used for implementing one or more embodiments of the present invention, in accordance with a computer implemented embodiment.

The present invention is advantageously implemented or, or assisted with on a computer. FIG. 8 is an illustration of a computer 858 used for implementing the computer processing in accordance with a computer-implemented embodiment of the present invention. The procedures described herein may be presented in terms of program procedures executed on, for example, a computer or network of computers.

Viewed externally in FIG. 8, computer 858 has a central processing unit (CPU) 868 having disk drives 869, 870. Disk drives 869, 870 are merely symbolic of a number of disk drives that might be accommodated by computer 858. Typically, these might be one or more of the following: a floppy disk drive 869, a hard disk drive (not shown), and a CD ROM or digital video disk, as indicated by the slot at 870. The number and type of drives varies, typically with different computer configurations. Disk drives 869, 870 are, in fact, options, and for space considerations, may be omitted from the computer system used in conjunction with the processes described herein.

Computer 858 also has a display 871 upon which information may be displayed. The display is optional for the computer used in conjunction with the system described herein. A keyboard 872 and/or a pointing device 873, such as a mouse 873, may be provided as input devices to interface with central processing unit 868. To increase input efficiency, keyboard 872 may be supplemented or replaced with a scanner, card reader, or other data input device. The pointing device 873 may be a mouse, touch pad control device, track ball device, or any other type of pointing device.

Figure 10:
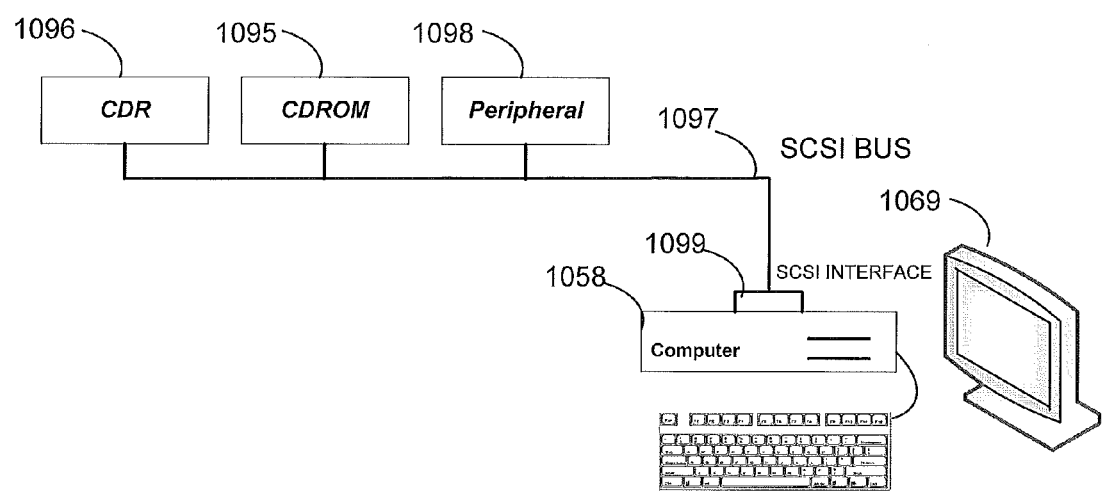
FIG. 10 illustrates a block diagram of an alternative computer of a type suitable for carrying out the present invention.

Alternatively, referring to FIG. 10, computer 1058 may also include a CD ROM reader 1095 and CD recorder 1096, which are interconnected by a bus 1097 along with other peripheral devices 1098 supported by the bus structure and protocol. Bus 97 serves as the main information highway interconnecting other components of the computer. It is connected via an interface 1099 to the computer 1058.

Figure 9:
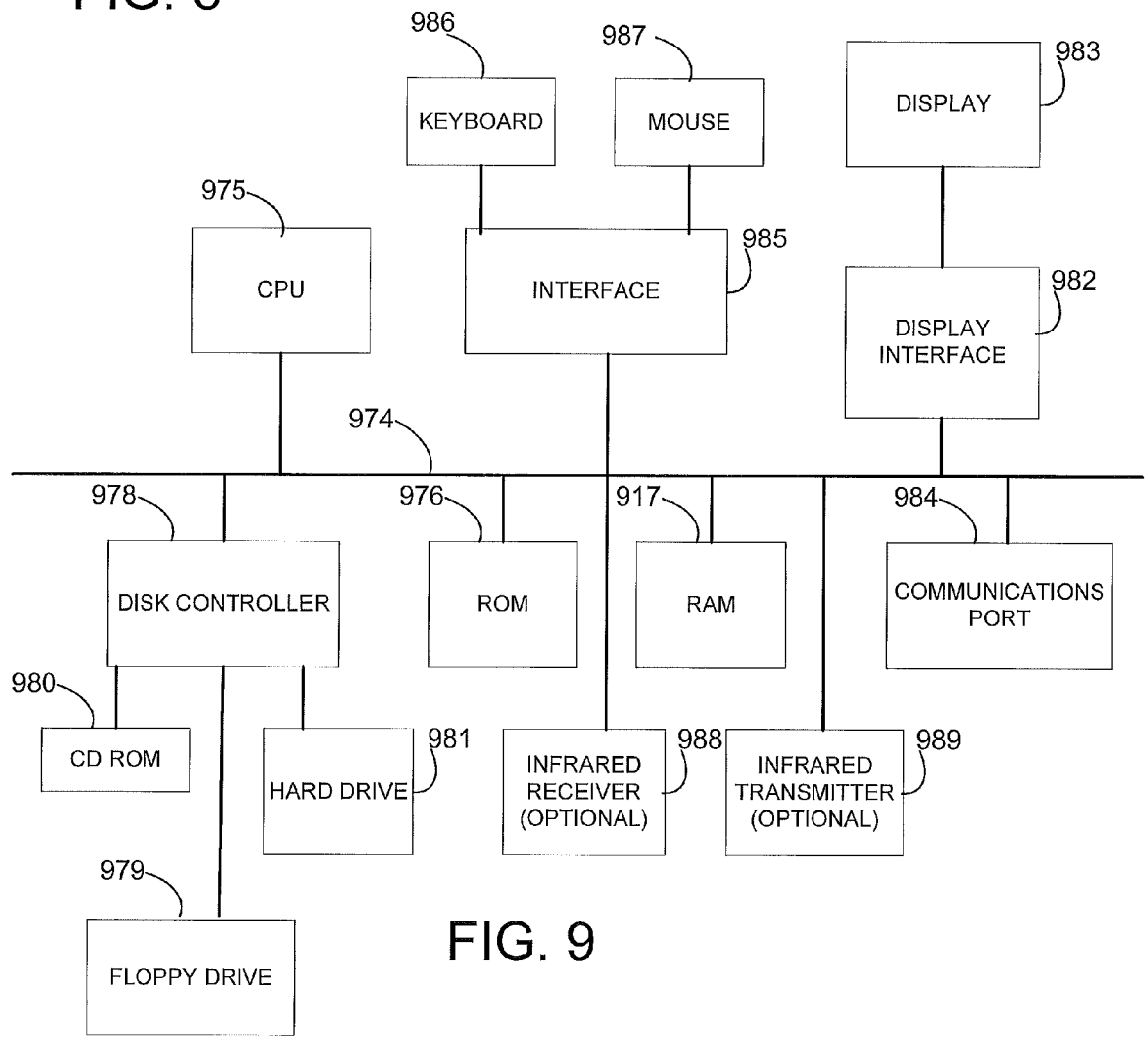
FIG. 9 illustrates a block diagram of the internal hardware of the computer of FIG. 8.

FIG. 9 illustrates a step diagram of the internal hardware of the computer of FIG. 8. CPU 975 is the central processing unit of the system, performing calculations and logic operations required to execute a program. Read only memory (ROM) 976 and random access memory (RAM) 977 constitute the main memory of the computer. Disk controller 978 interfaces one or more disk drives to the system bus 974. These disk drives may be floppy disk drives such as 979, or CD ROM or DVD (digital video/versatile disk) drives, as at 980, or internal or external hard drives 981. As previously indicated these various disk drives and disk controllers are optional devices.

A display interface 982 permits information from bus 974 to be displayed on the display 983. Again, as indicated, the display 983 is an optional accessory for a central or remote computer in the communication network, as are infrared receiver 988 and transmitter 989. Communication with external devices occurs using communications port 984.

In addition to the standard components of the computer, the computer may also include an interface 985, which allows for data input through the keyboard 986 or pointing device, such as a mouse 987.

The system according to the invention may include a general purpose computer, or a specially programmed special purpose computer. The user may interact with the system via e.g., a personal computer or over PDA, e.g., the Internet, an intranet, etc. Either of these may be implemented as a distributed computer system rather than a single computer. Similarly, the communications link may be a dedicated link, a modem over a POTS line, and/or any other method of communicating between computers and/or users. Moreover, the processing could be controlled by a software program on one or more computer systems or processors, or could even be partially or wholly implemented in hardware.

Further, this invention has been discussed in certain examples as if it is made available to a single user. The invention may be used by numerous users, if preferred. The system used in connection with the invention may rely on the integration of various components including, as appropriate and/or if desired, hardware and software servers, database engines, and/or other content providers.

Although the computer system in FIG. 8 is illustrated as having a single computer, the system according to one or more embodiments of the invention is optionally suitably equipped with a multitude or combination of processors or storage devices. For example, the computer may be replaced by, or combined with, any suitable processing system operative in accordance with the principles of embodiments of the present invention, including sophisticated calculators, hand held, laptop/notebook, mini, mainframe and super computers, as well as processing system network combinations of the same. Further, portions of the system may be provided in any appropriate electronic format, including, for example, provided over a communication line as electronic signals, provided on floppy disk, provided on CD Rom, provided on optical disk memory, etc.

Any presently available or future developed computer software language and/or hardware components can be employed in such embodiments of the present invention. For example, at least some of the functionality mentioned above could be implemented using Visual Basic, C, C++ or any assembly language appropriate in view of the processor being used. It could also be written in an interpretive environment such as Java and transported to multiple destinations to various users.

As another example, the system may be a general purpose computer, or a specially programmed special purpose computer. It may also be implemented to include a distributed computer system rather than as a single computer; some of the distributed system might include embedded systems. Similarly, the processing could be controlled by a software program on one or more computer systems or processors, or could be partially or wholly implemented in hardware.

As another example, the system may be implemented on a web based computer, e.g., via an interface to collect and/or analyze data from many sources. It may be connected over a network, e.g., the Internet, an Intranet, or even on a single computer system. Moreover, portions of the system may be distributed (or not) over one or more computers, and some functions may be distributed to other hardware, and still remain within the scope of this invention. The user may interact with the system via e.g., a personal computer or over PDA, e.g., the Internet, an intranet, etc. Either of these may be implemented as a distributed computer system rather than a single computer. Similarly, a communications link may be a dedicated link, a modem over a POTS line, and/or any other method of communicating between computers and/or users. Moreover, the processing could be controlled by a software program on one or more computer systems or processors, or could even be partially or wholly implemented in hardware.

User interfaces may be developed in connection with an HTML display format. It is possible to utilize alternative technology for displaying information, obtaining user instructions and for providing user interfaces.

The system used in connection with the invention may rely on the integration of various components including, as appropriate and/or if desired, hardware and software servers, database engines, and/or other process control components. The configuration may be, alternatively, network-based and may, if desired, use the Internet as an interface with the user.

The system according to one or more embodiments of the invention may store collected information in a database. An appropriate database may be on a standard server, for example, a small Sun™ Sparc™ or other remote location. The information may, for example, optionally be stored on a platform that may, for example, be UNIX-based. The various databases may be in, for example, a UNIX format, but other standard data formats may be used. The database optionally is distributed and/or networked.

Although the system is illustrated as having a single computer, the system according to one or more embodiments of the invention is optionally suitably equipped with a multitude or combination of processors or storage devices. For example, the computer may be replaced by, or combined with, any suitable processing system operative in accordance with the principles of embodiments of the present invention, including sophisticated calculators, hand held, laptop/notebook, mini, mainframe and super computers, one or more embedded processors, as well as processing system network combinations of the same. Further, portions of the system may be provided in any appropriate electronic format, including, for example, provided over a communication line as electronic signals, provided on floppy disk, provided on CD ROM, provided on optical disk memory, etc.

The invention may include a process and/or steps. Where steps are indicated, they may be performed in any order, unless expressly and necessarily limited to a particular order. Steps that are not so limited may be performed in any order.

To confirm the advantages of the present invention, experiments were carried out on actual data. The first aggregation method, which was based on geographic proximity, was applied to an actual patient database. This aggregation scheme resulted in about the same number of zip areas (889) as under the HIPAA "safe harbor" rules (875), which recommends 3 digit zip codes. More importantly, while not significantly affecting the overall risk, it resulted in a dramatic reduction in maximum risk as the table below shows.

| % Unique records when applied to actual patient database | | | |
|---|---|---|---|
| | Average Risk | Minimum Risk | Maximum Risk |
| HIPAA "Safe Harbor" aggregation | .78% | .00% | 9.61% |
| Zip code aggregation | .77% | .36% | 1.14% |

The second aggregation method, which was based on aggregation across medical information, was run on approximately 700 million actual prescription drug claims made during the 2000-2001 year. This aggregation scheme, applied to the 4 level hierarchy, ideally produces 81 different types of zip codes. There are 3 different levels for each of the four meta-clusters, which results in 3×3×3×3=81 types. At this level of aggregation, the method results in only 148 unique age type pairs, or 0.00024% of the population. This means when age, gender, and zip code are the only fields in a record matched to a public use data file, aggregation based on drug usage can conform to HIPAA "safe harbor" when providing birth year, birth month, and gender. Further, ages over 90 do not need to be re-coded or aggregated in the de-identified microdata file. This demonstrates that aggregation based on drug usage can preserve useful information, while dramatically reducing re-identification risk in accordance with the embodiments of the present invention.

The many features and advantages of the embodiments of the present invention are apparent from the detail specification, and thus, it is intended by the appended claims to cover all such features and advantages of the invention that fall within the true spirit and scope of the invention. Further, since numerous modifications and variations were readily occurred to those skilled in the art, it is not desired to limit the invention to the exact construction and operation illustrated and described, and accordingly, all suitable modifications and equivalents maybe resorted to, falling within the scope of the invention.

What is claimed is:

1. A method comprising:
    associating, on a computer processor, purchases of a plurality of prescription drugs into a plurality of second-level categories of a formulary therapeutic classification scheme;
    grouping, on the computer processor, the plurality of second-level categories into a plurality of third-level clusters based on points of similarities among the plurality of second-level categories, a total number of the plurality of third-level clusters being less than half of the total number of the second-level categories;
    grouping, on the computer processor, the plurality of third-level clusters into a plurality of fourth-level clusters, a total number of the plurality of fourth-level clusters being less than half of the total number of the third-level clusters;
    grouping, on the computer processor, the plurality of fourth-level clusters into four meta-clusters, the four-meta-clusters including an acute meta-cluster, a chronic meta-cluster, a dermatological meta-cluster, and a miscellaneous meta-cluster, a cluster hierarchy including the plurality of second-level categories, the plurality of third-level clusters, the plurality of fourth-level clusters, and the four meta-clusters;
    associating, on the computer processor, each of a plurality of zip codes with a plurality of paths in the cluster hierarchy, a path of the plurality of paths including a single second-legal category, a single third-level cluster, a single fourth-level cluster, and a single meta-cluster of the cluster hierarchy;
    retrieving, on the computer processor, a plurality of patient profile records and a corresponding patient medical information for each zip code of the plurality of zip codes, the patient medical information including prescription purchases, current medical conditions, genetic traits, or combinations thereof associated with at least some of a plurality of patients identified in the plurality of patient profile records;
    determining, on the computer processor, a number of instances in each zip code that the plurality of patients bought a prescription drug based on the plurality of patient profile records and the corresponding patient medical information to calculate prescription drug usage;

comparing, on the computer processor, calculated prescription drug usage in each of the plurality of zip codes to expected prescription drug usage in each of the plurality of zip codes to categorize usage in each of the plurality of zip codes as being a high usage, an average usage, or a low usage;

receiving, on the computer processor, a request to identify a geographic area with a particular level of drug usage;

determining, on the computer processor, a particular path in the cluster hierarchy with which requested drug usage has been associated;

retrieving, on the computer processor and using the path in the cluster hierarchy, the level of the requested drug usage for a geographic area, the geographic area covering at least some of the plurality of zip codes; and generating, on the computer processor, a response based on the particular level of the drug usage for the geographic area.

2. The method of claim 1, wherein grouping the plurality of second-level categories comprises:
using an agglomerative clustering algorithm to group the plurality of second-level categories into the plurality of third-level clusters.

3. A non-transitory machine-readable medium comprising instructions, which when executed by one or more processors, cause the one or more processors to perform the following operations:
associate purchases of a plurality of prescription drugs into a plurality of second-level categories of a formulary therapeutic classification scheme;

group the plurality of second-level categories into a plurality of third-level clusters based on points of similarities among the plurality of second-level categories, a total number of the plurality of third-level clusters being less than half of the total number of the second-level categories;

group the plurality of third-level clusters into a plurality of fourth-level clusters, a total number of the plurality of fourth-level clusters being less than half of the total number of the third-level clusters;

group the plurality of fourth-level clusters into four meta-clusters, the four-meta-clusters including an acute meta-cluster, a chronic meta-cluster, a dermatological meta-cluster, and a miscellaneous meta-cluster, a cluster hierarchy including the plurality of second-level categories, the plurality of third-level clusters, the plurality of fourth-level clusters, and the four meta-clusters;

associate each of a plurality of zip codes with a plurality of paths in the cluster hierarchy, a path of the plurality of paths including a single second-legal category, a single third-level cluster, a single fourth-level cluster, and a single meta-cluster of the cluster hierarchy;

retrieve a plurality of patient profile records and a corresponding patient medical information for each zip code of the plurality of zip codes, the patient medical information including prescription purchases, current medical conditions, genetic traits, or combinations thereof associated with at least some of a plurality of patients identified in the plurality of patient profile records;

determine a number of instances in each zip code that the plurality of patients bought a prescription drug based on the plurality of patient profile records and the corresponding patient medical information to calculate prescription drug usage;

compare calculated prescription drug usage in each of the plurality of zip codes to expected prescription drug usage in each of the plurality of zip codes to categorize usage in each of the plurality of zip codes as being a high usage, an average usage, or a low usage;

receive a request to identify a geographic area with a particular level of drug usage;

determine a particular path in the cluster hierarchy with which requested drug usage has been associated;

retrieve, using the path in the cluster hierarchy, the level of the requested drug usage for a geographic area, the geographic area covering at least some of the plurality of zip codes; and generate a response based on the particular level of the drug usage for the geographic area.

* * * * *